United States Patent [19]

Kubo et al.

[11] Patent Number: 4,859,468

[45] Date of Patent: Aug. 22, 1989

[54] COMPOSITIONS AND METHOD FOR DECOMPOSING ADIPOSE TISSUE

[75] Inventors: Michinori Kubo, Sakai; Reiko Matsuda, Osaka, both of Japan

[73] Assignee: Senju Pharmaceutical Co., Ltd., Osaka, Japan

[21] Appl. No.: 914,681

[22] Filed: Oct. 2, 1986

[30] Foreign Application Priority Data

Oct. 3, 1985 [JP] Japan ................................ 60-220934
Oct. 3, 1985 [JP] Japan ................................ 60-220935

[51] Int. Cl.⁴ ............................................. A61K 35/78
[52] U.S. Cl. .................................. 424/195.1; 514/909; 426/648
[58] Field of Search ...................... 424/195.1; 514/909; 426/648, 845

[56] References Cited

PUBLICATIONS

Wren, Potter's Cyclopedia, p. 45, 1950.
King, "American Dispensatory"; pp. 642–643, 1870.
Bioactive Natural Substances, pp. 390–395 (1978), with English translation.
Die Pflanzenstoffe, pp. 198–199 (1930).

*Primary Examiner*—John W. Rollins
*Attorney, Agent, or Firm*—Armstrong, Nikaido, Marmelstein, Kubovcik & Murray

[57] ABSTRACT

Solvent extracts of *Piper angustifolium* and/or *Boldea fragrans* have excellent adipose tissue decomposing activity.

These extracts, if administered in appropriate drug forms, provide effective remedy of corpulent constitution and if these extracts are added to any food or beverage, their ingestion enables control of overweight.

4 Claims, No Drawings

COMPOSITIONS AND METHOD FOR DECOMPOSING ADIPOSE TISSUE

BACKGROUND OF THE INVENTION

The present invention relates to a method for controlling overweight and to health maintaining compositions having adipose tissue decomposing ability and particularly, pertains to therapeutic compositions for preventing obesity and food or beverage compositions for controlling overweight.

Females and males of middle or advanced age have a deep concernn about control of overweight or therapy of obesity for esthetic and health reasons.

Consumption of oolong tea is considered preferable for control of overweight and for therapy of obesity. Also, limiting ingestion of meals, snacks and beverages is practiced for controlling excessive intake of calories.

Of the conventional methods of controlling overweight, consumption of oolong tea may indirectly contribute to control of overweight since the oolong tea is not sweet in itself. But it is not clear that oolong tea has a positive overweight controlling effect. Also, it is not easy for persons who are inured to taking stimulating beverages such as coffee and cola to switch to oolong tea only, abstaining from all of these beverages.

The approach of limiting the ingestion of meals, snacks and beverages, etc., may be the most sure way for controlling overweight or preventing obesity, but such a practice of ingestion limiting is often difficult to exercise for a long time because of the extreme pain accompanying it.

An object of this invention is to provide a method for controlling overweight.

Another object of this invention is to provide an adipose tissue decomposing composition useful for preventing overweight or further, for therapy of obesity or hyperlipidemia.

A further object of this invention is to provide a consumable composition which does not cause overweight and, moreover, enable treatment of obesity, when served as edible or potable supplies.

SUMMARY OF THE INVENTION

The method for controlling overweight of this invention consists essentially of administering orally to a patient an effective overweight controlling amount of solvent extracts of *Piper angustifolium* and/or *Boldea fragrans*.

The adipose tissue decomposing compositions of this invention comprise as their effective ingredients solvent extracts of *Piper angustifolium* and/or *Boldea fragrans*.

As these extracts are administered in drug forms, effective mobilization of free fatty acids from the adipose tissue will take place, enabling attainment of goal of preventing overweight or therapy of obesity or hyperlipidemia.

The consumable compositions having overweight controlling ability of this invention consist essentially of food or beverage and solvent extracts of *Piper angustifolium* and/or *Boldea fragrans*.

By ingesting the consumable compositions of this invention, control of overweight and further, therapy of obesity may be realized without a painful feeling of hunger.

DETAILED DESCRIPTION OF THE INVENTION

*Piper angustifolium* and *Boldea fragrans* are the plant materials used in this invention. Details of their growing districts and effects are described below.

These plants are known for various effects, but their overweight controlling or obesity preventing effect has not yet been reported and their addition to any food or beverage has not yet been attempted.

(1) *Piper angustifolium*

*Piper angustifolium* is a plant belonging to the family Piperaceae, and is commonly called MATICO. The plant itself or its parts including dried parts such as leaves, stems, roots or other parts are hereinafter referred to inclusively or severally, as the case may be, as "MATICO".

MATICO grows mainly in South America and is normally used as a hemostyptic. A decoction made of MATICO is effective for curing thoracic and laryngeal diseases, pneumonia, laryngitis, etc., and has also curing effects against hematocephalus, dysentery, diarrhea and tenesmus. Taking a bath in a decoction of MATICO is recommended as a cure for female's congestion of the brain, menstrual disorder, uterine sore and menstrual colic and also for leucorrhea.

(2) *Boldea fragrans*

*Boldea fragrans* is a plant belonging to the family Nyctaginaceae, and is commonly called BOLDO. The plant itself or its parts including dried parts such as leaves, stems, roots or other parts are hereinafter referred to inclusively or severally, as the case may be, as "BOLDO".

BOLDO naturally grows in Chile in South America. It is cultivated also in Brazil and is famous as a medicinal herb. BOLDO leave preparation is known to be effective against chalanopoiesis and acute or chronic hepatitis and has diuretic activity.

The effective ingredients from MATICO and BOLDO can be obtained by extracting them from their leaves, stems, buds, etc., especially from leaves, using organic or inorganic solvents. After extraction procedure, the solvent extracts may be oridnarily subjected to drying to remove the solvents substantially, preferably completely. Examples of the organic solvents used are alcohols such as methanol, ethanol or propanol, ethers, esters, ketones, etc., and water is used as the inorganic solvent. Extracts with hot water and/or ethanol are most preferable because of their high adipose tissue decomposing and obesity preventing effects.

The above-mentioned extracts may be therapeutically utilized as adipose tissue decomposing compositions.

Drug forms

The extracts may be used in any of the conventional manners employed in the medicinal use of plant ingredients. The preparation of this invention may be formulated making use of pharmaceutical carriers or excipients which are conventionally employed for the formulation of plant extract into drug forms. Examples of drug forms are:

(a) Tablets, powder or capsules for oral administration.

They may contain such usual excipients as binders (syrup, gum arabic, gelatin, sorbitol, tragacanth, polyvinyl pyrrolidone, etc.), vehicles (milk sugar, sugar, corn starch, calcium phosphate, sorbitol, glycine, etc.), lubricants (magnesium stearate, talc, polyethylene glycol, silica, etc.), disintegrators (potato starch, etc.) and wetting agents (sodium lauryl sulfate, etc.). Tablets may be coated with any appropriate materials by any suitable methods.

(b) Oral liquid medicinal preparations.

They may be aqueous or oily suspensions, solutions, syrups, elixirs, etc., or they may be in dry form which is to be redissolved with water or some appropriate vehicle before use.

These liquid medicinal preparations may contain such commonly used additives as suspension forming agents (sorbitol syrups, methylcellulose, sugar syrup, gelatin, hydroxyethylcellulose, carboxymethylcellulose, aluminum stearate gel, hydrogenated edible oil, etc.), emulsifiers (lecithin, sorbitan monooleate, gum arabic, etc.), nonaqueous vehicles (almond oil, fractionated coconut oil, oily esters, propylene glycol, ethyl alcohol, etc.), and disinfectants (p-hydroxymethyl benzoate, p-hydroxypropyl benzoate, sorbic acid, etc.).

(c) Compositions for injection.

They may be in the forms of suspension, solution, emulsion in oily or aqueous vehicles and may contain such additives as suspension forming agents, stabilizers and dispersants. The active ingredients may be powders to be redissolved with appropriate vehicles, for example, sterilized water, not containing exothermic materials.

(d) Tea bag form.

They may be supplied in the form of dried leaf slit of MATICO and/or BOLDO packed in a bag such as one made of non-woven cloth to be extracted with hot water before use.

Dosages

The dosage may be selected from wide ranges. For example, it is often set from a fraction of 1 gram to several grams, particularly, 1.0–2.0 g, as the net amount of extract per one day for an adult. Generally, continuous administration of small amounts at a time for long periods (for example, from several weeks to several months or further, several years) is desirable.

Toxicity

Extracts of MATICO and BOLDO give a high degree of safety, and do not show any acute toxicity as described below:

Leaves of MATICO and BOLDO were respectively extracted with hot water, concentrated under reduced pressure after filtration and then, freeze-dried. Into ICR male mice (24–26 g) which had fasted for 12 hr, 2 g/kg (nearly the maximum administrable amount) of the extract of MATICO and the extract of BOLDO, respectively, were orally administered once, to conduct an acute toxicity test of MATICO and BOLDO. The behavior of the mice including any death within 24 hr were observed as indices. In the seven cases tested, no death of the mice was observed within 24 hr. No specifically notable abnormal behavior was recognized in any mice.

Consumable compositions having overweight controlling activity

The extracts may be added to food or beverage to provide edible and potable supplies.

Illustrated as food or beverage are sweet comestibles (biscuit, chewing gum, candy, drop, caramel, jelly, marshmallow, sponge cake, cream puff, pie, doughnut, hot cake, ice cream, sherbet, cookie, etc.), breads, alcoholic drinks (sake, liquor, beer, fruit wine, Chinese liquor, spiced wine, etc.), coffee, black tea, cocoa, soft drinks, fruit juices, dairy products (milk, lactic acid beverage, acidophilus drink, butter, cheese, condensed milk, etc.), edible oils and fats, (vegetable oil and fat, mineral oil and fat, margarine, etc.), seasonings (bean paste, soy sauce, sauce, ketchup, dressing, refined sugar, honey, artificial sweeteners, chemical seasonings, etc.), spices and processed foodstuffs of various types (ham, sausage, canned and bottled foods, food boiled in soy, noodles, jam, marmalade, soybean milk, curry rice premixes, soup stocks, seasoning powder, etc.).

The amount of the extracts of MATICO and/or BOLDO to be added to food or beverage in proportion thereto is not particularly limited, but if it is too small, the overweight controlling effect can not be obtained; on the other hand, if too large, there will be the possibility of altering the original flavors of the food or beverage. Normally, the extracts are added in a range of 0.0001–10 parts by weight, particularly, 0.001–1 part by weight on dry base, to 100 parts by weight of food or beverage. When the amount added is at an appropriate level, the flavors of food or beverage sometimes will be rather improved.

MATICO and/or BOLDO may be added to food or beverage at any stage—in the raw material, or while processing or cooking.

Solvents extracts of MATICO and BOLDO show evident adipose tissue decomposing activity. Their decomposition accelerating activity is far superior as compared with that of oolong tea which has hitherto been believed to have relatively large effect.

Therefore, administration of the extracts in appropriate drug forms will provide an effective remedy against corpulent constitution or hyperlipidemia.

The addition of the extracts to food or beverage will enable effective mobilization of free fatty acids from the adipose tissue after such articles have been ingested, thus contributing to control of overweight and further, therapy of obesity. Accordingly, control of overweight will be achieved without a painful feeling of hunger.

By making optimal choice of the amount of the extracts added to the food or beverage, the original flavors will not be impaired at all; contrarily, sometimes, such flavors may be upgraded.

The extracts are obtained from natural plants and are considered highly safe, having no acute toxicity as described above.

EXAMPLE

The following examples illustrate the invention. All parts are by weight.

Preparation of extracts

Extracts were taken from 10 parts by weight of dry MATICO leaves with 1000 parts by weight of a 70% aqueous solution of ethanol, concentrated under reduced pressure after filtration and then, freeze-dried. The same procedure was carried out using a hot water instead of 70% aqueous solution of ethanol. The 70% ethanol aqueous solution extract and the hot water extract thus obtained were tested.

Similarly, extracts were taken from 10 parts by weight of dry BOLDO leaves with 1000 parts by weight of a 70% aqueous solution of ethanol, concentrated under reduced pressure after filtration and then, freeze-dried. The same procedure was carried out using a hot water instead of the 70% aqueous solution of ethanol. The 70% ethanol aqueous solution extract and the hot water extract thus obtained were tested.

For comparison, leaves of CEDRON (*Lippia citriodora, Sima cedron*), CHANCAPIEDRA (*Phyllanthus niruri*) and MOLLE (*Davana dependens*), medicinal herbs produced in South America, and leaves of oolong tea produced in China and Japanese tea were also similarly subjected to extraction, filtration and then, freeze-drying. The extracts were tested.

Yields of specimens obtained by extraction were as follows. In this table, EtOH represents ethanol.

| Specimen | Yield |
| --- | --- |
| 70% EtOH Aqueous solution extract of MATICO | 9.4% |
| 70% EtOH Aqueous solution extract of BOLDOO | 18.3% |
| 70% EtOH Aqueous solution extract of CEDRON | 12.3% |
| 70% EtOH Aqueous solution extract of CHANCAPIEDRA | 6.4% |
| 70% EtOH Aqueous solution extract of MOLLE | 13.6% |
| Hot water extract of MATICO | 17.3% |
| Hot water extract of BOLDO | 24.6% |
| Hot water extract of CEDRON | 21.7% |
| Hot water extract of oolong tea | 19.4% |
| Hot water extract of Japanese tea (green tea) | 25.0% |

(A) Activity on free fat cell

Activity of these extracts on free fat cell was tested in accordance with Rodbell's method (M. Rodbell, J. Biol. Chem., 239, 375 (1964)).

Eight grams of fat tissue at epididymis of male Wister rat (body weight 150–200 g) was sliced and was added into 20 ml of a Krebs-Ringer phosphoric acid buffer solution (pH 7.4) (hereinafter referred to as KRP buffer solution) containing 20 mg of glucose, 4% of bovine serum albumin and 20 mg of collagenase. The mixture was incubated at 37° C. for 50 min, and after filtration with nylon mesh, was centrifuged at 500 rpm for 30 sec; then, any portion that was not the fat cell layer was sucked out. The fat cell layer was washed twice with the KRP buffer solution and then diluted to 20 ml by addition of the KRP buffer solution. To 0.25 ml of this suspension, 0.5 ml of KRP buffer solution containing 5% of bovine serum albumin and 0.1 ml of the liquids to be tested or KRP buffer solution as control were added; these mixtures were incubated at 37° C. for 2 hr and the freed fatty acids were assayed by Dole's method (V. P. Dole, J. Clin. Invest., 35, 150 (1956)).

The results are shown in Table 1.

TABLE 1

| | | Concentration ($\mu$g/ml) | Number of tests | Free fatty acid($\mu$Eq/g) |
| --- | --- | --- | --- | --- |
| ☆ | Buffer solution | — | 5 | 1.23 ± 0.34 |
| * | 70% EtOH extract of MATICO | 100 | 5 | 9.26 ± 0.60 |
| * | 70% EtOH extract of MATICO | 200 | 5 | 3.78 ± 0.79 |
| * | 70% EtOH extract of BOLDO | 100 | 5 | 1.48 ± 0.25 |
| * | 70% EtOH extract of BOLDO | 200 | 5 | 11.64 ± 2.85 |
| # | 70% EtOH extract of CEDRON | 100 | 5 | 1.56 ± 0.17 |
| # | 70% EtOH extract of CEDRON | 200 | 5 | 1.78 ± 0.23 |
| # | 70% EtOH extract of CHANCAPIEDRA | 100 | 5 | 2.44 ± 0.13 |
| # | 70% EtOH extract of CHANCAPIEDRA | 200 | 5 | 2.59 ± 0.22 |
| # | 70% EtOH extract of MOLLE | 100 | 5 | 2.98 ± 0.16 |
| # | 70% EtOH extract of MOLLE | 200 | 5 | 3.74 ± 0.59 |
| ☆ | Buffer Solution | — | 9 | 3.46 ± 0.17 |
| * | Hot water extract of MATICO | 100 | 5 | 7.90 ± 0.36 |
| * | Hot water extract of MATICO | 200 | 5 | 14.66 ± 0.47 |
| * | Hot water extract of BOLDO | 100 | 5 | 8.21 ± 0.26 |
| * | Hot water extract of BOLDO | 200 | 5 | 14.66 ± 0.52 |
| # | Hot water extract of CEDRON | 100 | 5 | 3.39 ± 0.10 |
| # | Hot water extract of CEDRON | 200 | 5 | 3.39 ± 0.10 |
| # | Hot water extract of oolong tea | 100 | 5 | 4.11 ± 0.26 |
| # | Hot water extract of oolong tea | 200 | 5 | 4.62 ± 0.26 |
| # | Hot water extract of Japanese tea (green tea) | 100 | 5 | 4.44 ± 0.26 |
| # | Hot water extract of Japanese tea (green tea) | 200 | 5 | 5.83 ± 0.18 |

Note:
Mark ☆ designates control.
Mark * designates examples.
Mark # designates comparative examples.

It is understood from the above result that when 100 $\mu$g/ml or 200 $\mu$g/ml of the test specimens reacted with free fatty acids, mobilization of free fatty acids from free fat cell is distinctively recognized in the 70% aqueous ethanol solution extract of MATICO and hot water extract of the same and in the 70% aqueous ethanol solution extract of BOLDO and hot water extract of the same. In the hot water extracts of oolong tea and Japanese tea (comparative examples) mobilization of free fatty acids from free fat cell was observed, but this effect is considered to be very small, as compared with that of MATICO and BOLDO.

(B) Activity on the adrenaline's decomposing action on free fat cell

To the suspension obtained by the above-mentioned method (A), adrenaline was further added with the liquids to be tested or KRP buffer solution as control to have a final concentration of 0.5 $\mu$g/ml and the amounts of the freed fatty acids were assayed.

The results are shown in Table 2.

TABLE 2

| | | Concentration ($\mu$g/ml) | Number of tests | Free fatty acid ($\mu$Eq/g) |
| --- | --- | --- | --- | --- |
| ☆ | Buffer solution | — | 5 | 13.99 ± 1.55 |
| * | 70% EtOH extract of MATICO | 200 | 5 | 18.18 ± 0.39 |
| * | 70% EtOH extract of BOLDO | 200 | 5 | 14.15 ± 3.34 |

TABLE 2-continued

|   | | Concentration (μg/ml) | Number of tests | Free fatty acid (μEq/g) |
|---|---|---|---|---|
| # | 70% EtOH extract of CHANCAPIEDRA | 200 | 5 | 8.75 ± 0.40 |
| # | 70% EtOH extract of MOLLE | 200 | 5 | 9.06 ± 0.20 |
| ☆ | Buffer solution | — | 5 | 23.58 ± 1.63 |
| * | Hot water extract of MATICO | 100 | 5 | 25.32 ± 0.36 |
| * | Hot water extract of MATICO | 200 | 5 | 26.55 ± 0.26 |
| * | Hot water extract of BOLDO | 100 | 5 | 25.42 ± 0.30 |
| * | Hot water extract of BOLDO | 200 | 5 | 26.34 ± 0.61 |

Note:
Mark ☆ designates control.
Mark * designates examples.
Mark # designates comparative examples.

It is understood from the above result that free fatty acid is freed when 0.5 μg/ml of adrenaline is acted on free fat cell.

When the 70% ethanol aqueous solution extract of MATICO and hot water extract of the same and those of BOLDO are acted on the mixture, it is observed that the liberation of free fatty acids by adrenaline is enhanced.

However, when the 70% ethanol aqueous solution extracts of CHANCAPEDRA and MOLLE are acted on this mixture, it is observed that the liberation of the free fatty acids by adrenaline tends to decrease.

Restraining action on Body weight increases

Wistar rats aged 6 weeks were divided into 4 groups of 10 rats each. To the rats of the first group, the normal feed; to the rats of the second group, the normal feed mixed with 1.0% of the hot water extract of MATICO; to the rats of the third group, the normal feed mixed with 1.0% of the hot water extract of BOLDO; and to the rats of the fourth group, the feed mixed with 1.0% of the hot water extract of oolong tea, were given respectively. Body weight increases in these rats were measured after 2 months.

The results are shown below. Thus a distinctive restraining effect on body weight increase was confirmed when the feed mixed with MATICO and the feed mixed with BOLDO were given to the rats.

| Mean body weight increment per one rat: | |
|---|---|
| Rats in the first group | 156 ± 11 g |
| Rats in the second group | 144 ± 16 g |
| Rats in the third group | 146 ± 13 g |
| Rats in the fourth group | 151 ± 9 g |

Examples of pharmaceutical preparations

Tablets and powder were prepared by the conventional methods from the following formulations:

| (a) Tablets for oral administration | |
|---|---|
| Lactose | 50 mg |
| Corn starch | 15 mg |
| Polyvinyl pyrrolidone | 5 mg |
| Magnesium stearate | 1 mg |
| Talc | 1 mg |
| Hot water extract of MATICO (or hot water extract of BOLDO) | 50 mg |
| (b) Powder for oral administration | |
| Microcrystalline cellulose | 400 mg |
| Hydroxypropylcellulose | 100 mg |
| Silicic acid anhydride | 200 mg |
| Starch | 120 mg |
| 70% ethanol aqueous solution extract of MATICO (or 70% ethanol aqueous solution extract of BOLDO) | 200 mg |
| (c) Tablets for oral administration | |
| Milk sugar | 60 mg |
| Potato starch | 20 mg |
| Polyvinyl pyrrolidone | 5 mg |
| Magnesium stearate | 1 mg |
| Talc | 1 mg |
| Hot water extract* of MATICO (or hot water extract* of BOLDO) | 60 mg |

*Concentrated extract before freeze-drying was used.

Examples of preparing consumable composition

Consumable compositions were prepared by the conventional methods from the following formulations:

| (a) Candy | |
|---|---|
| Sugar | 70 parts |
| Malt syrup | 25 parts |
| Agar-agar | 5 parts |
| Hot water extract of MATICO (or hot water extract of BOLDO) | 0.1 part |
| (b) Chewing gum | |
| Polyvinyl acetate | 20 parts |
| Ester gum | 2 parts |
| Polyisobutylene | 4 parts |
| Calcium carbonate | 4 parts |
| Glucose | 25 parts |
| Powdered sugar | 45 parts |
| Hot water extract of MATICO (or hot water extract of BOLDO) | 0.5 part |
| (c) Bread | |
| Wheat flour | 100 parts |
| Yeast | 2 parts |
| Sodium chloride | 2 parts |
| Sugar | 3 parts |
| Shortening oil | 3 parts |
| Water | 56 parts |
| Hot water extract of MATICO (or hot water extract of BOLDO) | 0.2 part |
| (d) Noodle | |
| Flour of medium tackiness | 100 parts |
| Water | 35 parts |
| Sodium chloride | 4 parts |
| 70% ethanol aqueous solution extract of MATICO (or 70% ethanol aqueous solution of BOLDO) | 0.2 part |
| (e) Carbonated beverage | |
| Carbonated beverages available on the market (sugar, honey, vitamins, citric acid, malic acid, and amino acid) | 100 parts |
| Hot water extract* of MATICO (or hot water extract* of BOLDO) | 0.3 part |
| (f) Milk | |
| Milk available on the market | 100 parts |
| Hot water extract of MATICO (or hot water extract of BOLDO) | 0.3 part |
| (g) | Chocolate |
| Cocoa mass | 15 parts |
| Cocoa butter | 20 parts |
| Whole milk powder | 20 parts |
| Skim milk powder | 5 parts |

| | |
|---|---|
| Milk sugar | 40 parts |
| Hot water extract of MATICO (or hot water extract of BOLDO) | 0.8 part |

*Concentrated extract before freeze-drying was used.

We claim:

1. A method for controlling overweight comprising giving orally to an overweight human subject an effective overweight controlling amount of an extract of at least one plant selected from the group consisting of *Piper angustifolium* and *Boldea fragrans*.

2. A method according to claim 1 wherein said extract is an extract in at least one solvent selected from the group consisting of an organic solvent and hot water.

3. A method according to claim 2 wherein the organic solvent is ethanol.

4. A consumable composition having overweight controlling activity, consisting essentially of:
   (a) an extract of at least one plant selected from the group consisting of *Piper angustifolium* and *Boldea fragrans*; and
   (b) a food or beverage component selected from the group consisting of sweet comestibles, breads, alcoholic drinks, coffee, black tea, cocoa, soft drinks, fruit juices, dairy products, edible oils and fats, seasonings, spices and processed foodstuffs, p1 wherein the amount of said extract is 0.001–1 part by weight on a dry basis to 100 parts by weight of the food or beverage component.

* * * * *

UNITED STATES PATENT AND TRADEMARK OFFICE
CERTIFICATE OF CORRECTION

PATENT NO.    :    4,859,468
DATED         :    August 22, 1989
INVENTOR(S) :     KUBO et al It is certified that error appears in the above-identified patent and that said Letters Patent is hereby corrected as shown below:

Column 10, line 14, "pl" should be deleted.

Signed and Sealed this

Twenty-first Day of August, 1990

Attest:

HARRY F. MANBECK, JR.

*Attesting Officer*    *Commissioner of Patents and Trademarks*